United States Patent
Tzannis et al.

(10) Patent No.: US 7,192,919 B2
(45) Date of Patent: Mar. 20, 2007

(54) SUSTAINED RELEASE COMPOSITIONS FOR DELIVERY OF PHARMACEUTICAL PROTEINS

(76) Inventors: Stelios Tzannis, 32541 Wycombe Pl., Newark, CA (US) 94560; Nancy Dasovich, 55 Grattan St., San Francisco, CA (US) 94117; Sandeep Kumar, 474 Ives Ter., Sunnyvale, CA (US) 94087; Negar Sadrzadeh, 1104 Royal La., San Carlos, CA (US) 94070

(*) Notice: Subject to any disclaimer, the term of this patent is extended or adjusted under 35 U.S.C. 154(b) by 0 days.

(21) Appl. No.: 11/031,031

(22) Filed: Jan. 7, 2005

(65) Prior Publication Data
US 2005/0203002 A1 Sep. 15, 2005

Related U.S. Application Data

(60) Provisional application No. 60/535,185, filed on Jan. 7, 2004.

(51) Int. Cl.
*A61K 38/28* (2006.01)

(52) U.S. Cl. .......................................... 514/3; 530/304

(58) Field of Classification Search .................... None
See application file for complete search history.

(56) References Cited

U.S. PATENT DOCUMENTS

| | | | |
|---|---|---|---|
| 3,102,077 A | 8/1963 | Christensen | 530/304 |
| 4,667,668 A | 5/1987 | Wetterlin | 128/203.15 |
| 4,668,218 A | 5/1987 | Virtanen | 604/58 |
| 4,805,811 A | 2/1989 | Wetterlin | 222/337 |
| 5,320,094 A | 6/1994 | Laube et al. | 128/203.12 |
| 5,388,572 A | 2/1995 | Mulhauser et al. | 128/203.15 |
| 5,458,135 A | 10/1995 | Patton et al. | 128/200.14 |
| 5,522,385 A | 6/1996 | Lloyd et al. | 128/203.26 |
| 5,672,581 A | 9/1997 | Rubsamen et al. | 514/3 |
| 5,740,794 A | 4/1998 | Smith et al. | 128/203.15 |
| 5,785,049 A | 7/1998 | Smith et al. | 128/203.15 |
| 5,922,675 A | 7/1999 | Baker | 514/4 |
| 6,063,138 A | 5/2000 | Hanna et al. | 23/295 R |
| 6,309,671 B1 | 10/2001 | Foster et al. | 424/489 |
| 2004/0247870 A1* | 12/2004 | Brown et al. | 428/402 |

FOREIGN PATENT DOCUMENTS

| | | |
|---|---|---|
| EP | 0 129 985 | 9/1988 |
| EP | 0 467 172 | 4/1994 |

(Continued)

OTHER PUBLICATIONS

Edwards et al. Large Porous Particles for Pulmonary Drug Delivery. Science. Jun. 20, 1997, vol. 276, pp. 1868-1871.*

(Continued)

*Primary Examiner*—Jeffrey Edwin Russel
(74) *Attorney, Agent, or Firm*—Steven J. Helmer

(57) ABSTRACT

The present invention provides sustained release compositions that can be manufactured easily while providing long duration of the pharmaceutically useful protein being delivered. The compositions comprise insoluble complexes of the pharmaceutically useful protein and a precipitating agent at an appropriate ratio to achieve a desired sustained release profile. The precipitating agent can be selected from a group of various agents including divalent metal cations, Hofmeister series salts and pH adjusters. Particularly provided are compositions comprising insulin that are suitable for pulmonary delivery.

49 Claims, 3 Drawing Sheets

*In vitro dissolution of Zinc-Insulin Complexes*

FOREIGN PATENT DOCUMENTS

Figure 1:
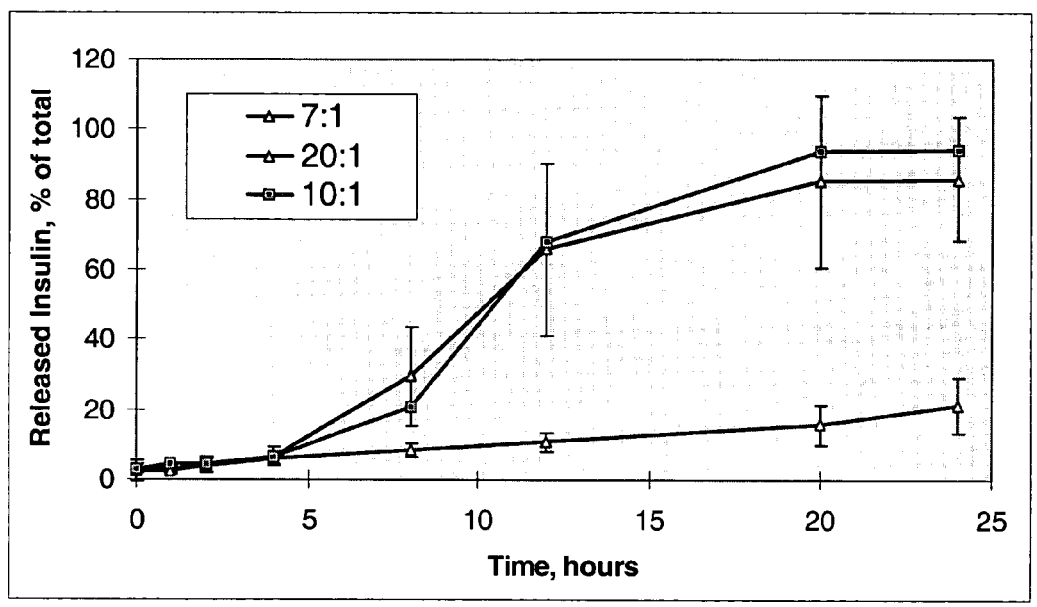

| | | |
|---|---|---|
| EP | 0 472 598 | 7/1996 |
| EP | 1 273 290 | 1/2003 |
| WO | 95/09616 | 4/1995 |
| WO | 96/32096 | 10/1996 |
| WO | 96/32149 | 10/1996 |
| WO | 97/41031 | 11/1997 |
| WO | 97/41833 | 11/1997 |
| WO | 98/16205 | 4/1998 |
| WO | 99/16419 | 4/1999 |
| WO | WO 99/66903 A2 * | 12/1999 |
| WO | 01/00674 | 1/2001 |
| WO | 01/32144 | 5/2001 |

OTHER PUBLICATIONS

Angell, "Formation of Glasses from Liquids and Biopolymers," Sci., 267:1924-1935, (Mar. 31, 1995).

Gibbs et al., "Nature of the Glass Transition and the Glassy State", The J. of Chem. Physics, 28(3):373-383, (Mar. 1958).

Gonda et al., "Physico-chemical principles in aerosol delivery", Medpharm Scientific Publishers Stuttgart; Topics in Pharm. Sci. 1991, Chapter 7, p. 95-115, (1992).

"Insulin", The United States Pharmacopeia USP 24. National Formulary NF 19, United States Pharmacopeial Convention, Rockville USA, pp. 883-887 (1999).

Kurtz et al., "Circulating IgG Antibody to Protamine in Patients Treated with Protamine-Insulins", Diabetologia 25:322-324, (1983).

Patton et al., "Inhaled Insulin", Advanced Drug Delivery Review, 35:235-247, (1999).

Samuel et al., "Studies on the immunogenicity of protamines in humans and experimental animals by means of a micro-complement fixation test", Clin. Exp. Immunol., 33:252-260, (1978).

Vanbever et al., "Sustained Release of Insulin from Insoluble Inhaled Particles", Drug Development Research, 48:178-185, (1999).

Wolanczyk, "Differential Scanning Calorimetry Analysis of Glass Transitions", Cryo-Letters, 10:73-76, (1989).

Zeng et al., "The controlled delivery of drugs to the lung", International J. of Pharmaceutics, 124:149-164, (1995).

* cited by examiner

*In vitro* dissolution of Zinc-Insulin Complexes

SUSTAINED RELEASE COMPOSITIONS FOR DELIVERY OF PHARMACEUTICAL PROTEINS

This application claims the benefit U.S. Provisional Patent Application Ser. No. 60/535,185 filed on Jan. 7, 2004, which is incorporated herein by reference in its entirety.

FIELD OF THE INVENTION

This invention relates to sustained release compositions comprising insoluble complexes of pharmaceutically useful proteins and the use thereof. In particular, sustained release compositions of insulin are provided for pulmonary delivery.

REFERENCES

U.S. Pat. No. 6,309,671.
U.S. Pat. No. 6,063,138.
U.S. Pat. No. 5,785,049.
U.S. Pat. No. 5,740,794.
U.S. Pat. No. 5,672,581.
U.S. Pat. No. 5,522,385.
U.S. Pat. No. 5,458,135.
U.S. Pat. No. 5,388,572.
U.S. Pat. No. 5,320,094.
U.S. Pat. No. 4,805,811.
U.S. Pat. No. 4,668,218.
U.S. Pat. No. 4,667,668.
WO 01/32144.
WO 99/16419.
WO 98/16205.
WO 97/41031.
WO 97/41833.
WO 96/32149.
WO 96/32096.
WO 95/09616.
European Patent No. EP472598 (1996).
European Patent No. EP 467172 (1994).
European Patent No. EP 129985 (1988).
Angell, C. A., "Formation of Glasses from Liquids and Biopolymers", Science, 267, 1924–1935 (1995).
Gibbs and DiMarzio, "Nature of the Glass Transition and the Glassy State", Journal of Chemical Physics, 28, 373–383 (1958).
Gonda, "Physico-chemical principles in aerosol delivery," in Topics in Pharmaceutical Sciences 1991, Crommelin, D. J. and K. K. Midha, Eds, Medpharm Scientific Publishers, Stuttgart, pp. 95–115, 1992.
Kurtz, A. B. et al., "Circulating IgG antibody to protamine in patients treated with protamine-insulins", Diabetologia. 25(4), 322–324 (1983).
Masters, K., "Spray Drying Handbook", 5th ed., John Wiley & Sons, Inc., NY, N.Y. (1991).
Patton, et al., Adv. Drug Delivery Reviews, 1, 35 (2–3), 235–247 (1999).
"Physician's Desk Reference", 55th ed., Medical Economics, Montvale, N.J. (2001).
Remington: The Science & Practice of Pharmacy", 19th ed., Williams & Williams, (1995).
Samuel, T. et al., "Studies on the immunogenicity of protamines in humans and experimental animals by means of a micro-complement fixation test", Clin. Exp. Immunol. 33(2), 252–260 (1978).
Vanbever R. et al., "Sustained release of insulin from insoluble inhaled particles", Drug Dev. Res. 48, 178–185 (1999).
Wolanczyk, J. P., "Differential Scanning Calorimetry Analysis of Glass Transitions", Cryo-Letters, 10, 73–76 (1989).
Zeng, X. M., et al., "The controlled delivery of drugs to the lung", Int. J. Pharmaceutics 124, 149–164 (1995).

All of the above publications, patents and patent applications are herein incorporated by reference in their entirety to the same extent as if the disclosure of each individual publication, patent application or patent was specifically and individually indicated to be incorporated by reference in its entirety.

BACKGROUND OF THE INVENTION

Effective therapy for diabetes generally involves a combination of two types of exogenous insulin formulations due to fluctuations in the demand for insulin. A fast-acting meal time insulin formulation is used to dispose of meal-related blood glucose surge, and a sustained release formulation is employed to regulate the constant hepatic glucose output and maintain a basal insulin level. The sustained release formulation is typically injected several times a day at regular intervals. Unfortunately, many diabetics are unwilling to comply with this therapy due to the discomfort and inconvenience of multiple injections. Therefore, sustained release insulin formulations suitable for non-injection routes are desired.

Recently, delivery of therapeutics through pulmonary routes has proven to be advantageous for certain drugs. This approach eliminates the need for needles, limits irritation to the skin and body mucosa (common side effects of transdermally, iontophoretically, and intranasally delivered drugs), and eliminates the need for nasal and skin penetration enhancers (typical components of intranasal and transdermal systems that often cause skin irritations/dermatitis). Pulmonary administration is also economically attractive, amenable to patient self-administration, and is often preferred by patients over other alternative modes of administration.

Insulin is an ideal candidate for pulmonary delivery due to its relatively small molecular weight (about 5,800 daltons). However, the preparation of sustained release formulations for delivery to the lung is very challenging. In order to reach the alveoli in the deep lung, where absorption of drugs takes place, a drug is ideally delivered in relatively small particles, which tend not to deposit prematurely in the mouth, throat or upper airway. Furthermore, the drug should be delivered in a composition that releases its active ingredient in a sustained manner. Since small particles collectively contain a higher surface area than large particles of the same total mass, small particles release their ingredients faster than large particles. Therefore, the challenge in the preparation of sustained release pulmonary compositions is how to include an appropriate control mechanism in the small particles to slow down release of the drug.

A number of methods have been employed to control the release rate of drugs from pulmonary pharmaceutical compositions (see, e.g., Zeng et al., 1995). Examples of these methods include the use of liposomes or biodegradable microspheres, and modification of the drug so that the active form of the drug is not readily released. Another method is to include the drug in an insoluble complex. For example, the injectable sustained release insulin formulations often contain insulin in a crystallized form, which releases insulin more slowly than compositions comprising free insulin. The insulin crystals that exhibit a satisfactory sustained release profile in injectable compositions, however, are not suitable for pulmonary delivery, because the crystals are too big and deposit prematurely before they reach the deep lung.

Crystallization procedures that result in microcrystals have also been attempted to manufacture small crystals of insulin that can be delivered to the lung, but these procedures are complicated and tedious (WO 01/00674). Simple and effective methods of preparing sustained release compositions for pulmonary delivery are thus still desirable.

SUMMARY OF THE INVENTION

The present invention provides sustained release compositions tat can be manufactured easily while providing long duration of the pharmaceutical protein being delivered. The compositions comprise insoluble complexes of the pharmaceutical protein and a precipitating agent at an appropriate ratio to achieve a desired sustained release profile. The precipitating agent can be selected from a group of various agents including divalent metal cations, Hofmeister series salts and pH adjusters. By way of example, insulin can be precipitated with zinc chloride at a molar ratio of at least 6:1 (zinc to insulin), which results in an amorphous precipitate of insulin. Dry powder aerosol was prepared from the precipitate, and inhalation of the aerosol indicates that the composition can be effectively used as a sustained release composition.

Accordingly, one aspect of the present invention provides a sustained-release composition for pulmonary administration comprising an insoluble, amorphous complex comprising insulin and zinc, wherein the molar ratio of zinc to insulin in said composition is at least about 6:1. The molar ratio is more preferably at least about 10:1, yet more preferably at least about 15:1, and most preferably at least about 20:1.

Another aspect of the present invention provides compositions capable of providing sustained plasma levels of insulin for at least about 6 hours, more preferably at least about 7 hours, and yet more preferably at least about 8 hours, when administered to the lung of a mammalian subject.

Another aspect of the present invention provides a composition in aerosolized form, particularly in dry powder form, and more particularly a dry powder form prepared by spray drying. The particles of the dry powder preferably have a mass median diameter (MMD) from about 1 to about 5 microns. The mass median aerodynamic diameter (MMAD) of the particles is preferably less than about 10 microns, more preferably less than about 5 microns, and most preferably less than about 3.3 microns. The emitted dose of the dry powder compositions is preferably at least about 30% and more preferably at least about 40%.

Another aspect of the present invention provides compositions that comprise a pharmaceutically acceptable excipient. In one embodiment, the excipient is a glass-forming excipient. In another embodiment, the excipient is selected from the group consisting of carbohydrates, for example sugars. Other embodiments provide compositions comprising excipients selected from the group consisting of amino acids, amino acid dimers, amino acid trimers, and polyamino acids.

Another aspect of the present invention provides a method for preparing a sustained release composition useful for delivery of insulin to a mammal, comprising precipitating the insulin with zinc at a molar ratio of zinc to insulin of at least about 6:1.

Yet another aspect of the present invention provides a method of treating or ameliorating diabetes or related conditions comprising administering by inhalation a pharmaceutically effective amount of any composition of the present invention. In particular, the composition may be administered using a dry powder inhaler, a nebulizer, or a metered dose inhaler. The pharmaceutically effective amount may be administered in a single dose, or in a plurality of unit dosages.

BRIEF DESCRIPTION OF THE DRAWINGS

FIG. 1 shows the in vitro dissolution profiles of zinc-insulin complexes prepared at a zinc:insulin molar ratio of 7:1, 10:1, and 20:1, respectively.

FIG. 2 shows the plasma insulin levels over time resulting from administration of the 20:1 composition described in FIG. 1 (ZI-1), as compared to administration of an immediate release (IR) composition.

FIG. 3 shows the plasma C-peptide level, which is indicative of the level of endogenous insulin, following administration of the 20:1 composition.

DETAILED DESCRIPTION OF THE INVENTION

Definitions

The terms used in this disclosure are defined as follows unless otherwise indicated.

A "sustained release composition" is a composition that releases the active component slowly over a long period of time. In general, the active component is released over preferably at least about 3 hours, more preferably at least about 4 hours, still more preferably at least about 5 hours, even more preferably at least about 6 hours, and most preferably at least about 8 hours.

A substance is "amorphous" if particles of the substance possess no uniform shapes. In particular, a crystal substance is not amorphous.

A "protein" is an organic compound comprising one or more chains of amino acid residues linked by peptide bonds. As used herein, the term "protein" encompasses proteins of any length and derivatives thereof, such as peptides, glycopeptides, lipopeptides, glycoproteins and lipoproteins.

A "pharmaceutical protein" is a protein useful for pharmaceutical purposes.

A "sustained plasma level" of a protein for a specified period of time means that the protein can be detected in the plasma for a duration specified. A protein can be detected by any methods established in the art, e.g., immunological, biochemical or functional methods. For example, insulin can be detected by enzyme-linked immunosorbent assay, mass spectrometry, or determination of blood glucose levels.

A "precipitating agent" is a chemical compound or mixture of chemical compounds that is capable of precipitating a protein of interest when the agent is added to a solution of the protein. A protein can be precipitated by a variety of mechanisms, including but not limited to, affinity precipitation, salting out, and isoelectric precipitation.

An "insoluble complex" is a complex that does not dissolve in water, or a designated solvent where specified, in an hour. Typically, an insoluble complex has a solubility of less than about 30%, i.e., less than about 30% of the complex is dissolved in an hour. The insoluble complex has a solubility of preferably less than about 20%, more preferably less than about 10%, and most preferably less than about 5%.

"Insulin" as used herein includes proinsulin and encompasses any purified isolated polypeptide having part or all of the primary structural conformation (i.e., contiguous series of amino acid residues) and at least one of the biological properties of naturally occurring insulin. In general, the term "insulin" is meant to encompass natural and synthetically-derived insulin including glycoforms thereof as well as agonists and analogs thereof, including polypeptides having one or more amino acid modifications (deletions, insertions, or substitutions) to the extent that they substantially retain at least 80% or more of the therapeutic activity associated with full length insulin. Preferably, the polypeptides with amino acid modifications retain at least a 50% amino acid sequence identity with a native insulin. The insulins of the present invention may be produced by any standard manner, including but not limited to pancreatic extraction, recombinant expression and in vitro polypeptide synthesis.

A composition that is "suitable for pulmonary delivery" refers to a composition that is capable of being aerosolized and inhaled by a subject so that a portion of the aerosolized particles reaches the lungs to permit penetration into the alveoli. Such a composition is considered to be "respirable" or "inhaleable".

An "aerosolized" composition contains liquid or solid particles that are suspended in a gas (typically air), typically as a result of actuation (or firing) of an inhalation device such as a dry powder inhaler, an atomizer, a metered dose inhaler, or a nebulizer.

A "nebulizer" is a device that forces compressed air through a solution of a drug so that a fine spray can be delivered to a facemask and inhaled. Nebulizers are often used to administer drugs to those who lack the ability to use a metered-dose or breath-activated inhaler.

A "dry powder inhaler" is a device that is loaded with capsules of the drug in powder form. Generally the inhaler is activated by taking a breath; the capsule is punctured and the powder is dispersed so that it can be inhaled in "Spinhalers" or "Rotahalers". "Turbohalers" are fitted with canisters that deliver measured doses of the drug in powder form.

A "metered dose inhaler" or "MDI" is a device that delivers a measured dose of a drug in the form of a suspension of extremely small liquid or solid particles, which is dispensed from the inhaler by a propellant under pressure. Such inhalers are placed into the mouth and depressed (activated) to release the drug as the individual takes a breath.

"Emitted Dose" or "ED" provides an indication of the delivery of a drug composition from a suitable inhaler device after a firing or dispersion event. More specifically, for dry powder compositions, the ED is a measure of the percentage of powder which is drawn out of a unit dose package and which exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-determined parameter, and is typically determined using an in-vitro device set up which mimics patient dosing. To determine an ED value, a nominal dose of dry powder, typically in unit dose form, is placed into a suitable dry powder inhaler (such as that described in U.S. Pat. No. 5,785,049, assigned to Inhale Therapeutic Systems) that is then actuated, dispersing the powder. The resulting aerosol cloud is then drawn by vacuum from the device, where it is captured on a tared filter attached to the device mouthpiece. The amount of powder that reaches the filter constitutes the emitted dose. For example, for a 5 mg dry powder-containing dosage form placed into an inhalation device, if dispersion of the powder results in the recovery of 4 mg of powder on a tared filter as described above, then the emitted dose for the dry powder composition is: 4 mg (delivered dose)/5 mg (nominal dose)× 100 =80%. For non-homogenous powders, ED values are based on the amount of drug rather than on the total powder weight. They provide an indication of the amount of drug delivered from an inhaler device after firing rather than the amount of dry powder delivered. Similarly for MDI and nebulizer dosage forms, the ED corresponds to the percentage of drug which is drawn from a dosage form and which exits the mouthpiece of an inhaler device.

A composition in "dry powder form" is a powder composition that typically contains less than about 10% moisture.

"Mass median diameter", or "MMD", is a measure of mean particle size, since the powders of the present invention are generally polydisperse (i.e., consist of a range of particle sizes). MMD values can be determined by centrifugal sedimentation, or any other commonly employed technique for measuring mean particle size (e.g., electron microscopy, light scattering, laser diffraction).

"Mass median aerodynamic diameter", or "MMAD", is a measure of the aerodynamic size of a dispersed particle. The aerodynamic diameter is used to describe an aerosolized powder in terms of its settling behavior, and is the diameter of a unit density sphere having the same settling velocity, in air, as the particle. The aerodynamic diameter encompasses particle shape, density and physical size of a particle. As used herein, MMAD refers to the midpoint or median of the aerodynamic particle size distribution of an aerosolized powder determined by cascade impaction, unless otherwise indicated.

"Fine particle fraction" is the fraction of particles with an aerodynamic diameter that is less than 5 microns. Where specified, the fine particle fraction may also refer to the fraction of particles with an aerodynamic diameter that is less than 3.3 microns.

A "pharmaceutically acceptable excipient or carrier" refers to an excipient that may optionally be included in the compositions of the present invention. Preferred are excipients that can be taken into the lungs with no significant adverse toxicological effects to the subject, particularly to the lungs of the subject.

The "glass transition temperature (Tg)", as used herein, is the onset of a temperature range at which a composition changes from a glassy or vitreous state to a syrup or rubbery state. Generally Tg is determined using differential scanning calorimietry (DSC). The standard designation for Tg is the temperature at which onset of the change of heat capacity (Cp) of the composition occurs upon scanning through the transition. The definition of Tg, however, can be arbitrarily defined as the onset, midpoint or endpoint of the transition. For purposes of the present invention we will use the onset of the changes in Cp when using DSC and DER. See the article entitled "Formation of Glasses from Liquids and Biopolymers" by C. A. Angell: Science, 267, 1924–1935 (Mar. 31, 1995) and the article entitled "Differential Scanning Calorimetry Analysis of Glass Transitions" by Jan P. Wolanczyk: Cryo-Letters, 10, 73–76 (1989). For detailed mathematical treatment see "Nature of the Glass Transition and the Glassy State" by Gibbs and DiMarzio: Journal of Chemical Physics, 28, NO. 3, 373–383 (March, 1958). These articles are incorporated herein by reference.

A "glass-forming excipient" is an excipient that, when added to a composition, promotes glassy state formation of the composition.

The term "glass" or "glassy state", as used herein, refers to a liquid that has lost its ability to flow, i.e. it is a liquid with a very high viscosity, wherein the viscosity ranges from $10^{10}$ to $10^{14}$ pascal-seconds. It can be viewed as a metastable amorphous system in which the molecules have vibrational motion and reduced rotational motion, but have very slow (almost immeasurable by today's techniques) translational motion when compared to the liquid state. As a metastable system, it is stable for long periods of time when stored well below the glass transition temperature. Because glasses are not in a state of thermodynamic equilibrium, glasses stored at temperatures at or near the glass transition temperature relax to equilibrium upon storage and lose their high viscosity. The resultant rubbery or syrupy flowing liquid can lead to physical instability of the product. A solvent evaporation technique (U.S. Pat. No. 6,309,671) can be used to achieve a glassy state, as well as other processes that can produce a glassy state with acceptable Tg, for example, freeze drying followed by milling for micronization.

"Treating or ameliorating" a disease or medical condition means reducing or eliminating the symptoms of the disease or medical condition.

The term "diabetes and related conditions" refers to diseases or medical conditions caused by the lack or inaction of insulin. Diabetes and related conditions include type I and type II diabetes, particularly type I diabetes.

A "pharmacologically effective amount" or "physiologically effective amount" of a pharmaceutical composition is an amount sufficient for the intended purpose of the pharmaceutical composition. For example, an effective amount of a pharmaceutical composition to treat or ameliorate diabetes is an amount sufficient to reduce or eliminate the symptoms of diabetes, for example, an amount that is needed to provide a desired level of insulin in the bloodstream to result in a target blood glucose level. The pharmacologically effective amount of a given pharmaceutical composition will vary with factors such as the nature of the active component in the composition, the route of administration, the size and species of the animal to receive the composition, and the purpose of the administration. The suitable amount can be readily determined by one skilled in the art based upon available literature and the information provided herein.

Insoluble Complexes of the Present Invention

The present invention relates to the use of insoluble complexes of pharmaceutically useful proteins and precipitating agents to deliver the protein in a sustained release manner. Insulin is used as an example to demonstrate the practice and use of the present invention. As shown in Example 1, insulin was precipitated with zinc at increasing concentrations to prepare insulin-zinc complexes at a molar ratio of zinc to insulin of 7:1, 10:1 or 20:1. The complexes were tested in an in vitro dissolution assay to determine their dissolution kinetic profiles, and all of them yielded a slow and sustained release pattern of insulin (FIG. 1). The 20:1 complex was particular effective in providing sustained release and released only about 20% of insulin from the complexes after 24 hours. The 7:1 and 10:1 complexes were also capable of prolonged release, and gradually released about 85–90% of the insulin over a period of about 20 hours.

Figure 2:
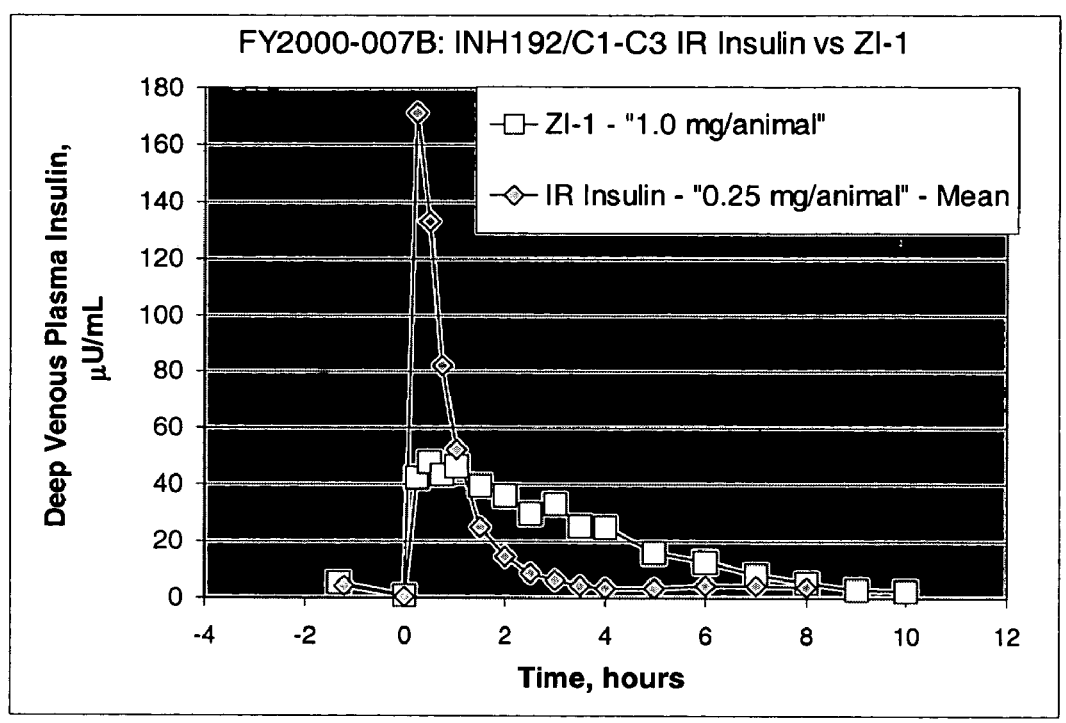
Figure 3:
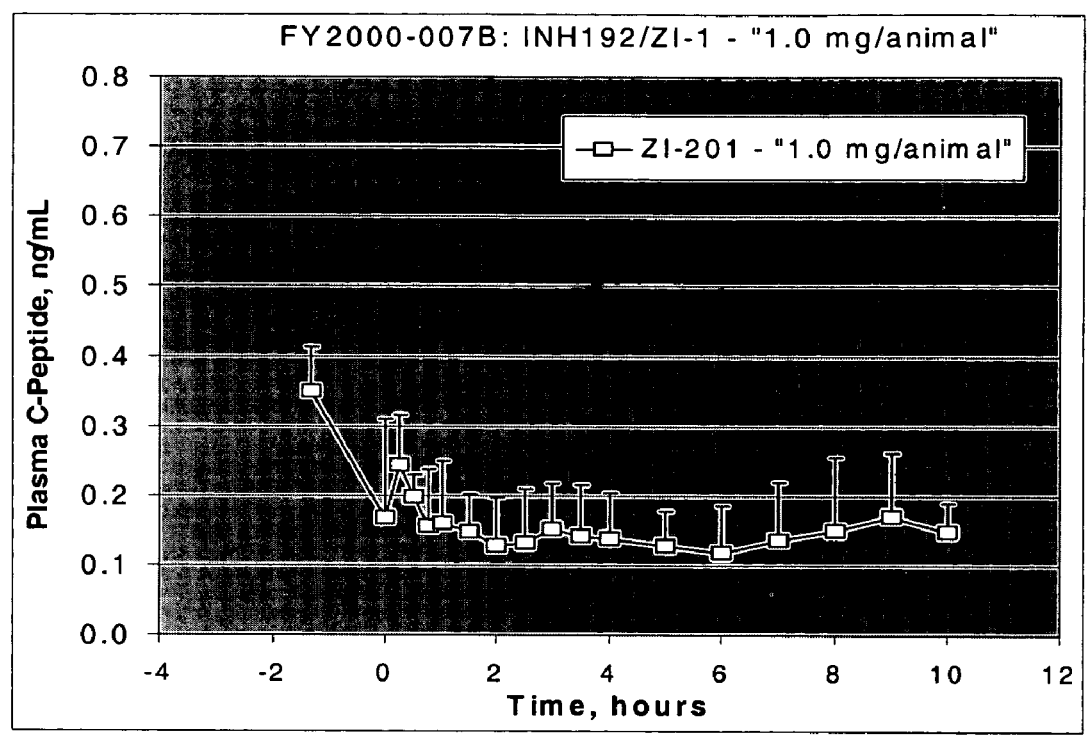

The 20:1 complexes were then manufactured as a dry powder composition and delivered to the lungs of test animals. An immediate release composition of insulin was also administered as a control, and the levels of plasma insulin were determined at various time points after administration (FIG. 2). The control composition resulted in a sharp peak of plasma insulin immediately after administration, followed by a sudden drop of plasma insulin to less than 10% of the peak level in about 2 hours. The level of plasma insulin then became undetectable in 3–4 hours post administration. In contrast, the insulin-zinc insoluble complexes continued to release insulin into the blood for about 10 hours, during which time the plasma insulin level was relatively steady. During these 10 hours, the insulin-producing β-cells were shut down, as indicated by the suppressed levels of C-peptide, indicating that the plasma insulin was entirely derived from exogenously administered insulin (FIG. 3). Therefore, the composition of the present invention is capable of delivering insulin in a sustained release manner and maintaining blood insulin level relatively stable.

Insulin has been found to form a crystal structure with zinc at a ratio of two or four zinc molecules to each insulin hexamer. The insulin-zinc complexes in the present invention, however, contain much more zinc and are amorphous rather than crystalline (Example 1). Without wishing to be limited to a theory, we believe that the high levels of zinc (or other precipitating agents) in the compositions of the present invention lead to the formation of "kinetically irreversible precipitates", which dissociate much more slowly than the insulin-zinc crystals described above. The term "kinetically irreversible" does not mean that the precipitation process is not reversible. Rather, it means that dissociation, with subsequent dissolution, is a slow process that is kinetically controlled.

The compositions of the present invention result in a detectable plasma level of the pharmaceutically useful protein that sustains for at least about 4 hours, preferably at least about 6 hours, more preferably at least about 7, 8, 9 or 10 hours, and most preferably at least about 12 hours or more. When compared to the crystalline insulin-zinc complexes containing 2 or 4 zinc molecules per each insulin hexamer, the compositions of the present invention result in a duration of plasma insulin that is preferably at least about 1.5 times, more preferably at least about 2 times, yet more preferably at least about 2.5 times, and most preferably at least about 3 times, that of the crystalline insulin-zinc composition.

The formation of the "kinetically irreversible" protein precipitates may be induced by a variety of ways. Examples include, but are not limited to: (a) affinity precipitation via complexation and specific interactions with appropriate cations, such as divalent cation salts (e.g., zinc, magnesium, calcium salts, both organic and inorganic); (b) salting out with Hofmeister series salts; (c) volume exclusion induced by addition of appropriate quantities of large polymers, such as polyethylene glycol (different molecular weights), dextran, etc.; and (d) isoelectric precipitation by a pH adjuster (acid or base).

Divalent metal cations, particularly zinc, are the preferred precipitating agents in the present invention. Proteins probably form insoluble complexes with these cations through predominantly surface-exposed histidine residues and, to a lesser extent, cysteine, tryptophan and glutamic acid residues. Zinc ions selectively precipitate proteins from solution by coordinating the lone pair electrons of heteroatoms on the side chains of these amino acids. Therefore, the present invention can be used to deliver proteins without limitation to the function, size, overall charge or physical properties of the proteins. The majority of the precipitation at low protein concentrations is thought to occur due to the interprotein crosslinking between metal-ion and free surface groups.

Precipitations using zinc are very rapid and are found to be kinetically irreversible. Protons in solution also compete with zinc ions for protein-binding sites; during the course of a metal precipitation there is usually a change in pH as protons are displaced from their coordination sites by the stronger binding zinc ions. This competitive binding offers possibilities for control of the kinetics of the dissolution process.

Preferred divalent metal ions include the transition metal, alkaline metal and alkaline earth metal ions. Transitional metal ions such as zinc, copper, cobalt and iron are particularly suitable. Zinc is the most preferred precipitating agent in the present invention.

It should be noted that the insulin-zinc complexes of the present invention are amorphous rather than crystalline. However, depending on the precipitation process, small amounts of crystals may exist in the compositions. Furthermore, the amorphous complexes of the present invention may be mixed with crystalline insulin-zinc complexes to make compositions with a mixed release feature. Accordingly, the compositions of the present invention may contain about one of the following dry weight percentages of amorphous complexes: 0%, 1%, 2%, 4%, 6%, 8%, 10%, 15%, 20%, 30%, 40%, 50%, 60%, 70%, 80% and 90%.

The Hofmeister series salts originated from the ranking of various ions in their ability to precipitate a mixture of hen egg white proteins. Anions of these salts include, for example, thiocyanide, nitrate, fluoride, chloride, bromine, iodine, citrate, acetate, phosphate, and sulfate. Cations of these salts include, for example, calcium, magnesium, sodium, potassium, ammonium, tetramethyl ammonium, cesium and aluminum. The relative ability of the salts to precipitate a given protein depends on the nature of the protein, pH and temperature, and can be experimentally determined.

The compositions of the present invention typically comprise the precipitating agent at a solid weight percentage of about 0.1% to about 95%, more preferably about 10% to about 85%, yet more preferably about 30% to about 75%, and most preferably about 50% to about 70%. The composition may comprise no precipitating agent, because when the pharmaceutically useful protein is precipitated by salting out, volume exclusion or isoelectric precipitation, the precipitating agent only facilitates precipitation, rather than forming part of the insoluble complex. Once the precipitates form, the precipitating agent may optionally be removed from the suspension, leaving no or only trace amount of the precipitating agent in the final composition. The addition of excipient may also change the percentage of the precipitating agent. Thus, depending upon the amount of excipient, a composition of the present invention will comprise the precipitating agent at a solid weight percentage of at least about one of the following: 0%, 10%, 15%, 20%, 30%, 40%, 50%, 60%, 70%, 80%, 90% or greater.

Any protein useful as a therapeutic agent can be delivered in an insoluble complex as described herein. The protein may also contain non-peptide moieties such as carbohydrate or lipid. Thus, these pharmaceutically useful proteins ("pharmaceutical proteins") of the present invention may include drugs which act on the peripheral nerves, adrenergic receptors, cholinergic receptors, the skeletal muscles, the cardiovascular system, smooth muscles, the blood circulatory system, synaptic sites, neuroeffector junctional sites, endocrine and hormone systems, the immunological system, the reproductive system, the skeletal system, autacoid systems, the alimentary and excretory systems, the histamine system, and the central nervous system. Suitable proteins may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The pharmaceutical protein may act locally or systemically.

Examples of pharmaceutical proteins suitable for use in this invention include but are not limited to calcitonin, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, respiratory syncytial virus antibody, deoxyreibonuclease (DNase), bactericidal/permeability increasing protein (BPI), anti-CMV antibody, and where applicable, analogues, agonists, antagonists, and inhibitors of the above, including the synthetic, native, glycosylated, unglycosylated, pegylated forms, and biologically active fragments and analogs thereof.

Compositions and corresponding doses of the pharmaceutical protein will vary with the bioactivity of the protein employed. For example, injectable insulin is measured in USP Insulin Units; one unit (U) of insulin is equal to the amount required to reduce the concentration of blood glucose in a fasting rabbit to 0.45 mg/ml (2.5 mM). Typical concentrations of insulin preparations for injection range from 30–100 Units/mL, which is about 3.6 mg of insulin per mL. The amount of insulin required to achieve the desired physiological effect in a patient will vary not only with the particulars of the patient and his disease (e.g., type I vs. type II diabetes) but also with the strength and particular type of insulin used. For instance, dosage ranges for regular insulin (rapid acting) are from about 0.3 to 2 U insulin per kilogram of body weight per day. The compositions of the present invention are, in one aspect, effective to achieve in patients undergoing therapy a fasting blood glucose concentration between about 90 and 140 mg/dl and a postprandial value below about 250 mg/dl. The precise dosages can be determined by one skilled in the art when coupled with the pharmacodynamics and pharmacokinetics of the precise insulin composition employed for a particular route of administration, and can readily be adjusted in response to periodic glucose monitoring.

Individual dosages (on a per inhalation basis) for inhaleable insulin compositions are typically in the range of from about 0.5 mg to 15 mg insulin, where the desired overall dosage is typically achieved in about 1–10 breaths, and preferably in about 1 to 4 breaths. On average, the overall dose of insulin administered by inhalation per dosing session will range from about 10 U to about 400 U, with each individual dosage or unit dosage form (corresponding to a single inhalation) containing from about 5 U to 400 U.

When the present invention is used to deliver insulin by inhalation to the lung, the amount of insulin in the composition will be that amount necessary to deliver a therapeutically effective amount of insulin per unit dose to achieve at least one of the therapeutic effects of native insulin, i.e., the ability to control blood glucose levels to near normoglycemia. In practice, this will vary widely depending upon the particular insulin, its activity, the severity of the diabetic condition to be treated, the patient population, the stability of the composition, and the like.

The composition will generally contain, in terms of solid weight, anywhere from about 1% to about 99%, typically from about 2% to about 95%, and more typically from about 5% to about 85% of the pharmaceutical protein. The percentage of the pharmaceutical protein in the composition will also depend upon the relative amounts of excipients/ additives contained in the composition. More specifically, the composition will typically contain at least about one of the following solid weight percentages of the pharmaceutical protein: 10%, 20%, 30%, 40%, 50%, 60%, 70%, 80%, 90% or more. Preferably, powder compositions will contain at least about 60%, e.g., about 60–100% by weight of the pharmaceutical protein. It is to be understood that more than one pharmaceutical protein may be incorporated into the compositions described herein. Furthermore, the composition may also contain more than one form of the pharmaceutical protein, for example two or more insulins.

The molar ratio of the precipitating agent to the pharmaceutical protein in the compositions of the present invention may range from about 1:1 to about 500:1. The ratio is more preferably from about 1:1 to about 100:1, even more preferably from about 1:1 to about 50:1, and most preferably from about 2:1 to about 20:1. The optimal molar ratio of the precipitating agent to the pharmaceutical protein may be determined by a person of ordinary skill in the art, and will generally be about one of the following: 1:1, 2:1, 3:1, 4:1, 5:1, 6:1, 7:1, 8:1, 9:1, 10:1, 15:1, 20:1, 30:1, 40:1, 50:1, 60:1, 70:1, 80:1, 90:1, 100:1 or greater.

One embodiment of the present invention provides compositions that contain no protamine. Protamines are a group of proteins isolated from fish, and are commonly used in insulin formulations to prolong duration (see, e.g., Vanbever et al., 1999). However, protamines, as well as protamine-insulin complexes, have been shown to be potentially immunogenic (Samuel et al., 1978; Kurtz et al., 1983). Since the compositions of the present invention are capable of sustained release in the absence of protamine, the present invention provides the option of including no protamine, thereby avoiding the adverse reactions that may be caused by protamine.

While the use of liposomes is also commonly employed to sustain duration of drug effect, the present invention does not require the use of liposomes. Similarly, polymers are often used to manufacture microspheres to encapsulate pharmaceutical agents for the purpose of delaying release of the pharmaceutical agents. The present invention can also be practiced without any polymer. Accordingly, other embodiments of the present invention provide compositions that contain no lipid, as well as compositions that contain no polymers, in addition to the pharmaceutical protein.

Excipients

The composition may further comprise excipients, solvents, stabilizers, etc., depending upon the particular mode of administration and dosage form. Preferred are carbohydrate excipients, either alone or in combination with other excipients or additives. Representative carbohydrates for use in the compositions of the present invention include sugars, derivatized sugars such as alditols, aldonic acids, esterified sugars, and sugar polymers. Exemplary carbohydrate excipients suitable for use in the present invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like. Preferred are non-reducing sugars, sugars that can form a substantially dry amorphous or glassy phase when combined with the composition of the present invention, and sugars possessing relatively high glass transition temperatures, or Tgs (e.g., Tgs greater than 40° C., preferably greater than 50° C., more preferably greater than 60° C., and even more preferably greater than 70° C., and most preferably having Tgs of 80° C. and above).

Additional excipients include amino acids, peptides and particularly oligomers comprising 2–9 amino acids, and more preferably 2–5 mers, and polypeptides, all of which may be homo or hetero species. Representative amino acids include glycine (gly), alanine (ala), valine (val), leucine (leu), isoleucine (ile), methionine (met), proline (pro), phenylalanine (phe), trytophan (trp), serine (ser), threonine (thr), cysteine (cys), tyrosine (tyr), asparagine (asp), glutamic acid (glu), lysine (lys), arginine (arg), histidine (his), norleucine (nor), and modified forms thereof. One particularly preferred amino acid is leucine.

Also preferred for use as excipients in inhaleable compositions are di- and tripeptides containing two or more leucyl residues, as described in Inhale Therapeutic System's International patent application WO 01/32144, incorporated herein by reference in its entirety.

Also preferred are di- and tripeptides having a glass transition temperature greater than about 40° C., more preferably greater than 50° C., even more preferably greater than 60° C., and most preferably greater than 70° C.

Although less preferred due to their limited solubility in water, additional stability and aerosol performance-enhancing peptides for use in the present invention are 4-mers and 5-mers containing any combination of amino acids as described above. More preferably, the 4-mer or 5-mer will comprise two or more leucine residues. The leucine residues may occupy any position within the peptide, while the remaining (i.e., non-leucyl) amino acids positions are occupied by any amino acid as described above, provided that the resulting 4-mer or 5-mer has a solubility in water of at least about 1 mg/ml. Preferably, the non-leucyl amino acids in a 4-mer or 5-mer are hydrophilic amino acids such as lysine, to thereby increase the solubility of the peptide in water.

Polyamino acids, and in particular, those comprising any of the herein described amino acids, are also suitable for use as stabilizers. Preferred are polyamino acids such as poly-lysine, poly-glutamic acid, and poly(lys, ala).

Additional excipients and additives useful in the present compositions and methods include but are not limited to proteins, non-biological polymers, and biological polymers, which may be present singly or in combination. Suitable excipients are those provided in Inhale Therapeutic Systems' International Publication Nos. WO 96/32096 and 98/16205. Preferred are excipients having glass transition temperatures above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. The compositions may also include a buffer or a pH-adjusting agent, typically but not necessarily a salt prepared from an organic acid or base. Representative buffers include organic acid salts of citric acid, ascorbic acid, gluconic acid, carbonic acid, tartaric acid, succinic acid, acetic acid, or phthalic acid. Other suitable buffers include Tris, tromethamine hydrochloride, borate, glycerol phosphate and phosphate. Amino acids such as glycine are also suitable.

The compositions of the present invention may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin.

The compositions may further include flavoring agents, taste-masking agents, inorganic salts (e.g., sodium chloride), antimicrobial agents (e.g., benzalkonium chloride), sweeteners, antioxidants, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, although preferably not in liposomal form), fatty acids and fatty esters, steroids (e.g., cholesterol), and chelating agents (e.g., zinc and other such suitable cations). The use of certain di-substituted phosphatidylcholines for producing perforated microstructures (i.e., hollow, porous microspheres) is described in greater detail below. Other pharmaceutical excipients and/or additives suitable for use in the compositions according to the present invention are listed in "Remington: The Science & Practice of Pharmacy", 19$^{th}$ ed., Williams & Williams, (1995), and in the "Physician's Desk Reference", 55th ed., Medical Economics, Montvale, N.J. (2001).

Preferred compositions in accordance with the present invention are absent penetration enhancers, which can cause irritation and are toxic at the high levels often necessary to provide substantial enhancement of absorption. Specific enhancers, which are typically absent from the compositions of the present invention, are the detergent-like enhancers such as deoxycholate, laureth-9, DDPC, glycocholate, and the fusidates. Certain enhancers, however, such as those that protect the pharmaceutical protein from enzyme degradation, e.g., protease and peptidase inhibitors such as alpha-1 antiprotease, captropril, thiorphan, and the HIV protease inhibitors, may, in certain embodiments of the present invention, be incorporated in the composition of the present invention. In yet another embodiment, the composition of the present invention is preferably absent liposomes, lipid matrices, and encapsulating agents.

Generally, the pharmaceutical compositions of the present invention will contain from about 1% to about 99% by weight excipient, preferably from about 5%–98% by weight excipient, more preferably from about 15–95% by weight excipient. Even more preferably, the spray-dried compositions will contain from about 0–50% by weight excipient, more preferably from 0–40% by weight excipient. In general, a high concentration of the pharmaceutical protein is desired in the final pharmaceutical composition. Typically, the optimal amount of excipient/additive is determined experimentally, i.e., by preparing compositions containing varying amounts of excipients (ranging from low to high), examining the chemical and physical stability of the pharmaceutical protein, MMADs and dispersibilities of the compositions, and then further exploring the range at which optimal aerosol performance is attained with no significant adverse effect upon the stability of the pharmaceutical protein.

Preparing Dry Powders

A preferred embodiment of the present invention provides dry powder compositions suitable for pulmonary delivery. Dry powder compositions of the present invention may be prepared by any of a number of drying techniques, and preferably by spray drying. Spray drying of the compositions is carried out, for example, as described generally in the "Spray Drying Handbook", 5$^{th}$ ed., K. Masters, John Wiley & Sons, Inc., NY, N.Y. (1991), and in Platz, R., et al., International Patent Publication Nos. WO 97/41833 (1997) and WO 96/32149 (1996), the contents of which are incorporated herein by reference.

Suspensions comprising the insoluble complexes of the present invention are spray-dried in a conventional spray drier, such as those available from commercial suppliers such as Niro A/S (Denmark), Buchi (Switzerland) and the like, resulting in a dispersible, dry powder. Optimal conditions for spray drying will vary depending upon the composition components, and are generally determined experimentally. The gas used to spray dry the material is typically air, although inert gases such as nitrogen or argon are also suitable. Moreover, the temperature of both the inlet and outlet of the gas used to dry the sprayed material is such that it does not cause degradation of the pharmaceutical protein in the sprayed material. Such temperatures are typically determined experimentally, although in general the inlet temperature will range from about 50° C. to about 200° C., while the outlet temperature will range from about 30° C. to about 150° C. Preferred parameters include atomization pressures ranging from about 20–150 psi, and preferably from about 30–40 to 100 psi. Typically the atomization pressure employed will be one of the following (psi): 20, 30, 40, 50, 60, 70, 80, 90, 100, 110, 120 or above.

Respirable compositions of the present invention having the features described herein may also be produced by drying certain composition components which result in formation of a perforated microstructure powder as described in WO 99/16419, assigned to Alliance Pharmaceutical Corporation, the entire contents of which are incorporated by reference herein. The perforated microstructure powders typically comprise spray-dried, hollow microspheres having a relatively thin porous wall defining a large internal void. The perforated microstructure powders may be dispersed in a selected suspension media (such as a non-aqueous and/or fluorinated blowing agent) to provide stabilized dispersions prior to drying. The use of relatively low density perforated (or porous) microstructures or microparticulates significantly reduces attractive forces between the particles, thereby lowering the shear forces, increasing the flowability and dispersibility of the resulting powders, and reducing the degradation by flocculation, sedimentation or creaming of the stabilized dispersions thereof.

Less preferably, powders may be prepared by lyophilization, vacuum drying, spray freeze drying, super critical fluid processing (e.g., as described in Hanna, et al., U.S. Pat. No. 6,063,138), air drying, or other forms of evaporative drying.

In yet another approach, dry powders may be prepared by agglomerating the powder components, sieving the materials to obtain agglomerates, spheronizing to provide a more spherical agglomerate, and sizing to obtain a uniformly sized product, as described, e.g., in Ahlneck, C., et al., International PCT Publication No. WO 95/09616, 1995, incorporated herein by reference.

Dry powders may also be prepared by blending, grinding, sieving or jet milling composition components in dry powder form.

Once formed, the dry powder compositions are preferably maintained under dry (i.e., relatively low humidity) conditions during manufacture, processing, and storage. Irrespective of the drying process employed, the process will preferably result in inhaleable, highly dispersible particles comprising the insoluble complexes of the present invention.

Features of Dry Powder Compositions

Preferred powders of the present invention are further characterized by several features, most notably, (i) consistently high dispersibilities, which are maintained, even upon storage, (ii) small aerodynamic particles sizes (MMADs), (iii) improved fine particle dose values, i.e., powders having particles sized less than 5 microns, all of which contribute to the improved ability of the powder to penetrate to the tissues of the lower respiratory tract (i.e., the alveoli) for delivery to the systemic circulation. These physical characteristics of the inhaleable powders of the present invention, to be described more fully below, are important in maximizing the efficiency of aerosolized delivery of such powders to the deep lung.

Dry powders of the present invention are composed of aerosolizable particles effective to penetrate into the lungs. As shown in Example 1, the amorphous insulin-zinc complexes of the present invention have a much smaller diameter (about 1 µm) than the insulin-zinc crystals (about 20 µm), and are thus superior for pulmonary delivery. The particles of the present invention may generally have a mass median diameter (MMD) of less than about 20 µm, preferably less than about 10 µm, more preferably less than about 7.5 µm, and most preferably less than about 4 µm, and even more preferably less than about 3.3 µm, and usually are in the range of 0.1 µm to 5 µm in diameter. Preferred powders are composed of particles having an MMD from about 1 to 5 µm. In some cases, the powder will also contain non-respirable carrier particles such as lactose, where the non-respirable particles are typically greater than about 40 microns in size.

The preferred powders of the present invention may also be characterized by an aerosol particle size distribution less than about 10 µm mass median aerodynamic diameter (MMAD), preferably having MMADs less than about 5 µm, more preferably less than about 4.0 µm, even more preferably less than 3.3 µm, and most preferably less than 3 µm. The mass median aerodynamic diameters of the powders will characteristically range from about 0.1–10 µm, preferably from about 0.2–5.0 µm MMAD, more preferably from about 1.0–4.0 µm MMAD, and even more preferably from about 1.5 to 3.0 µm. Small aerodynamic diameters are generally achieved by a combination of optimized spray drying conditions and choice and concentration of excipients.

The preferred powders of the present invention may also be characterized by their densities. The powder will generally possess a bulk density from about 0.1 to 10 g/cubic centimeter, preferably from about 0.1–2 g/cubic centimeter, and more preferably from about 0.15–1.5 g/cubic centimeter. In one embodiment of the present invention, the powders have big and fluffy particles with a density of less than about 0.4 g/cubic centimeter and an MMD between 5 and 30 microns. It is worth noting that the relationship of diameter, density and aerodynamic diameter can be determined by the following formula (Gonda, 1992):

$$\text{aerodynamic diameter} = \text{diameter} \sqrt{\text{density}}.$$

The powders will generally have a moisture content below about 20% by weight, usually below about 10% by weight, and preferably below about 5% by weight. Such low moisture-containing solids tend to exhibit a greater stability upon packaging and storage.

Additionally, the spray drying methods and stabilizers described herein are effective to provide highly dispersible compositions. Generally, the emitted dose (ED) of these powders is greater than 30%, and usually greater than 40%. More preferably, the ED of the powders of the present invention is greater than 50%, and is often greater than 60%.

The compositions described herein also possess good stability with respect to both chemical stability and physical stability, i.e., aerosol performance over time. Generally, with respect to chemical stability, the pharmaceutical protein contained in the composition will degrade by no more than about 10% upon spray drying. That is to say, the powder will possess at least about 90%, preferably at least about 95%, and even more preferably will contain at least about 97% or greater of the intact pharmaceutical protein. Preferably, the spray drying process will result in powders having less than about 10% total protein aggregates, that is to say, greater than 90% by weight of the pharmaceutical protein being in monomeric form.

With respect to aerosol performance, compositions of the present invention are generally characterized by a drop in emitted dose of no more than about 20%, preferably no more than about 15%, and more preferably by no more than about 10%, when stored under ambient conditions for a period of three months.

Administration of the Composition

The compositions of the present invention can be administered by any suitable route, such as pulmonary, intravascular, intramuscular, transdermal, subcutaneous, intraperitoneal and oral. The compositions are preferably administered pulmonarily, particularly by inhalation, and most particularly by inhalation of a dry powder composition.

The dry powder compositions as described herein may be delivered using any suitable dry powder inhaler (DPI), i.e., an inhaler device that utilizes the patient's inhaled breath as a vehicle to transport the dry powder drug to the lungs. Preferred are Inhale Therapeutic Systems' dry powder inhalation devices as described in Patton, J. S., et al., U.S. Pat. No. 5,458,135, Oct. 17, 1995; Smith, A. E., et al., U.S. Pat. No. 5,740,794, Apr. 21, 1998; and in Smith, A. E., et. al., U.S. Pat. No. 5,785,049, Jul. 28, 1998, herein incorporated by reference. When administered using a device of this type, the powdered medicament is contained in a receptacle having a puncturable lid or other access surface, preferably a blister package or cartridge, where the receptacle may contain a single dosage unit or multiple dosage units. Convenient methods for filling large numbers of cavities (i.e., unit dose packages) with metered doses of dry powder medicament are described, e.g., in Parks, D. J., et al., International Patent Publication WO 97/41031, Nov. 6, 1997, incorporated herein by reference.

Other dry powder dispersion devices for pulmonary administration of dry powders include those described, for example, in Newell, R. E., et al, European Patent No. EP 129985, Sep. 7, 1988); in Hodson, P. D., et al., European Patent No. EP472598, Jul. 3, 1996; in Cocozza, S., et al., European Patent No. EP 467172, Apr. 6, 1994, and in Lloyd, L. J. et al., U.S. Pat. No. 5,522,385, Jun. 4, 1996, incorporated herein by reference. Also suitable for delivering the dry powders of the present invention are inhalation devices such as the Astra-Draco "TURBUHALER". This type of device is described in detail in Virtanen, R., U.S. Pat. No. 4,668,218, May 26, 1987; in Wetterlin, K., et al., U.S. Pat. No. 4,667,668, May 26, 1987; and in Wetterlin, K., et al., U.S. Pat. No. 4,805,811, Feb. 21, 1989, all of which are incorporated herein by reference. Other suitable devices include dry powder inhalers such as Rotahaler® (Glaxo), Discus® (Glaxo), Spiros™ inhaler (Dura Pharmaceuticals), and the Spinhaler® (Fisons). Also suitable are devices which employ the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device, such as described in Mulhauser, P., et al, U.S. Pat. No. 5,388,572, Sep. 30, 1997, incorporated herein by reference.

The compositions of the present invention may also be delivered using a pressurized, metered dose inhaler (MDI), e.g., the Ventolin® metered dose inhaler, containing a solution or suspension of drug in a pharmaceutically inert liquid propellant, e.g., a chlorofluorocarbon or fluorocarbon, as described in Laube, et al., U.S. Pat. No. 5,320,094, Jun. 14, 1994, and in Rubsamen, R. M., et al, U.S. Pat. No. 5,672,581 (1994), both incorporated herein by reference.

Alternatively, the compositions described herein may be dissolved or suspended in a solvent, e.g., water or saline, and administered by nebulization. Nebulizers for delivering an aerosolized solution include the AERx™ (Aradigm), the Ultravent® (Mallinkrodt), the Pari LC Plus™ or the Pari LC Star™ (Pari GmbH, Germany), the DeVilbiss Pulmo-Aide, and the Acorn II® (Marquest Medical Products).

The following examples are offered to illustrate this invention and are not to be construed in any way as limiting the scope of the present invention.

EXAMPLES

In the examples below, the following abbreviations have the following meanings. Abbreviations not defined have their generally accepted meanings.

| | |
|---|---|
| ° C. = | degree Celsius |
| hr = | hour |
| min = | minute |
| μM = | micromolar |
| mM = | millimolar |
| M = | molar |

-continued

| | |
|---|---|
| ml = | milliliter |
| μl = | microliter |
| mg = | milligram |
| μg = | microgram |
| DPI = | dry powder inhaler |
| rpm = | rounds per minute |

Example 1

Formation of Insoluble Complexes by Affinity Precipitation

In order to examine the effect of insoluble complex formation on sustained release, we prepared precipitates of insulin using zinc chloride. The resulted compositions were spray dried, features of the dry powders were investigated, and the in vitro as well as in vivo insulin release profiles were determined.

Preparation of the Insulin-Zinc Compositions

Insulin was dissolved at 10 mg/mL in citrate buffer. Zinc chloride was added, under continuous stirring at 200–250 rpm, in such amounts as to achieve a Zn-to-insulin molar ratio of 7:1, 10:1 or 20:1. The compositions were spray-dried in a Buchi spray dryer model 190 under the following conditions: inlet temperature 135° C., outlet temperature 70° C., feed flow rate of 5 mL/min, air pressure of 60 psi, and compressed air flow rate of 17 L/min.

Particle Size Analysis

Light microscopy, laser diffraction and Horiba sedimentation were used to assess the primary particle size and size distribution of the spray-dried compositions. All compositions exhibited an average size around 1–1.5 μm and a tight distribution between 0.5–5 μm (the data for the 7:1 and 20:1 compositions are shown in Table I). The particles are amorphous rather than crystalline.

TABLE I

| | | Particle size | | | |
|---|---|---|---|---|---|
| Composition | Zn:Insulin Molar Ratio | Mean Diameter (μm) | MMAD (μm) | % <5 μm (%) | ED (%) |
| 1 | 7:1 | 1.5 | 2.6 | 88.5 ± 2.2 | 67.9 ± 2.2 |
| 2 | 20:1 | 1.2 | 3.1 | 79.3 ± 3.1 | 45.4 ± 3.1 |

Aerosol Properties

The aerodynamic and dispersion properties of the powders were examined via Andersen cascade impaction with an INHALE PDS model P2.3. The results are given in Table I and indicate the good dispersibility of the prepared powders. The dispersibility of these powders may be further improved by addition of appropriate amounts of suitable excipients, such as sugars, leucine and derivatives, and polyamino acids. For example, we have added leucine and polylysine to the compositions of the present invention and obtained powders with an MMAD of about 3 μm and an ED of about 90%.

In Vitro Dissolution Testing

The in vitro dissolution properties of the formulated powders were tested in an appropriately modified diafiltration system under sink conditions. The diafiltration system was used to remove the released zinc ions and facilitate dissolution of the precipitated insulin. In order to best mimic pulmonary delivery conditions, the particles were dispersed in a 0.5% w/v Tween-80 phosphate buffer (pH 6.9) in order to break agglomerates and ensure monomeric particle formation in solution. At selected time points, a sample was removed from a specially designed inlet port using a syringe. The sample was centrifuged at 14,0000 rpm for 14 minutes in order to separate un-dissolved particles from the released protein in the supernatant. The supernatants were assayed for insulin content using reversed-phase high pressure liquid chromatography (HPLC). In order to establish a mass balance, the samples were also dissolved by titration at low pH (pH<3) by addition of small amounts of HCl, and assayed for the total amount of insulin in the dissolution medium.

The results, expressed in percent released insulin over total insulin in the dissolution medium, are shown in FIG. 1. Thus, the 20:1 (zinc:insulin) composition released little insulin, indicating that the insulin-zinc complex was very stable and capable of releasing insulin over a long period of time (more than 24 hours under these conditions). The 10:1 and 7:1 compositions are also capable of sustained release of insulin.

In Vivo Testing

The in vivo dissolution properties of the 20:1 (zinc:insulin) composition were determined in a hypoglycaemic dog aerosol model using established methods. Briefly, the compositions were administered as aerosols to normal anaesthetized dogs. The animals' glucose levels were monitored throughout the study and their normoglycaemia state was maintained by intravenous injections of Dextrose 20%. Blood samples were withdrawn at appropriate time points, plasma was separated, and blood glucose, deep venous insulin and C-peptide levels were assayed using the plasma.

The deep venous insulin concentrations are shown in FIG. 2. In comparison to a control insulin powder containing zinc and insulin at a ratio of 2–4 zinc molecule to each insulin hexamer administered similarly in the same study, the 20:1 (zinc:insulin) composition exhibited a long absorption profile. Although the time to maximum plasma concentration (Tmax) did not change dramatically, the half-life of insulin was extended to approximately 3.5–4 hours. Elevated plasma insulin concentrations were detected until almost 8 hours post-administration, which is consistent with the duration of the glucose response of at least 8 hours.

Furthermore, the contribution of exogenous insulin was confirmed by assay of the C-peptide levels in the dog plasma. As shown in FIG. 3, upon administration of the insulin-zinc composition, the C-peptide levels dropped, indicating a shutdown of the β-cells as well as the endogenous insulin production mechanisms. The C-peptide levels remained low for at least 8 hours, indicating that the insulin detected in the plasma was entirely due to exogenously administered insulin.

Taken together, these results indicate that pulmonarily delivered compositions comprising insoluble complexes of insulin and zinc are capable of releasing insulin over a prolonged time period, and the released insulin acts to regulate blood glucose level in the absence of endogenous insulin.

Variations and equivalents of this example will be apparent to those of skill in the art in light of the present disclosure, the drawings and the claims herein.

All articles, books, patents and other publications referenced herein are hereby incorporated by reference in their entirety.

We claim:

1. A sustained release composition comprising an insoluble, amorphous complex comprising insulin and zinc, wherein the molar ratio of zinc to insulin in said composition is at least about 6:1, wherein said composition comprises a powder comprising particles having a mass median aerodynamic diameter (MMAD) of less than about 10 microns.

2. The composition of claim 1 wherein the molar ratio of zinc to insulin in said composition is at least about 10:1.

3. The composition of claim 1 wherein the molar ratio of zinc to insulin in said composition is at least about 15:1.

4. The composition of claim 1 wherein the molar ratio of zinc to insulin in said composition is at least about 20:1.

5. The composition of claim 1 wherein the composition provides sustained plasma levels of insulin for at least about 6 hours when administered to the lung of a mammalian subject.

6. The composition of claim 1 wherein the composition provides sustained plasma levels of insulin for at least about 7 hours when administered to the lung of a mammalian subject.

7. The composition of claim 1 wherein the composition provides sustained plasma levels of insulin for at least about 8 hours when administered to the lung of a mammalian subject.

8. The composition of claim 1, wherein the powder comprises a dry powder.

9. The composition of claim 8 wherein the dry powder is prepared by spray drying.

10. The composition of claim 8 wherein the dry powder comprises particles having a mass median diameter (MMD) from about 1 to about 5 microns.

11. The composition of claim 8 wherein the dry powder comprises particles having a mass median aerodynamic diameter (MMAD) of less than about 5 microns.

12. The composition of claim 8 wherein the dry powder comprises particles having a mass median aerodynamic diameter (MMAD) of less than about 3.3 microns.

13. The composition of claim 8 with an emitted dose of at least about 30%.

14. The composition of claim 8 with an emitted dose of at least about 40%.

15. The composition of claim 1, in aerosolized form.

16. The composition of claim 1 further comprising a pharmaceutically acceptable excipient.

17. The composition of claim 16 wherein the excipient is a glass-forming excipient.

18. The composition of claim 16 wherein the excipient is a carbohydrate.

19. The composition of claim 18 wherein the carbohydrate is a sugar.

20. The composition of claim 16 wherein the excipient is selected from the group consisting of amino acids, amino acid dimers, amino acid trimers, and polyamino acids.

21. A method for preparing a sustained release composition, comprising precipitating insulin with zinc at a molar ratio of zinc to insulin of at least about 6:1 to form insoluble, amorphous complexes of insulin and zinc, wherein said composition comprises a powder comprising particles having a mass median aerodynamic diameter (MMAD) of less than about 10 microns.

22. The method of claim 21 wherein the molar ratio of zinc to insulin in said composition is at least about 10:1.

23. The method of claim 21 wherein the molar ratio of zinc to insulin in said composition is at least about 15:1.

24. The method of claim 21 wherein the molar ratio of zinc to insulin in said composition is at least about 20:1.

25. The method of claim 21 wherein the composition provides sustained plasma levels of insulin for at least about 6 hours when administered to the lung of a mammalian subject.

26. The method of claim 21 wherein the composition provides sustained plasma levels of insulin for at least about 7 hours when administered to the lung of a mammalian subject.

27. The method of claim 21 wherein the composition provides sustained plasma levels of insulin for at least about 8 hours when administered to the lung of a mammalian subject.

28. The method of claim 21 wherein the powder comprises a dry powder.

29. The method of claim 28 wherein the dry powder is prepared by spray drying.

30. The method of claim 28 wherein the dry powder comprises particles having a mass median diameter (MMD) from about 1 to about 5 microns.

31. The method of claim 28 wherein the dry powder comprises particles having a mass median aerodynamic diameter (MMAD) of less than about 5 microns.

32. The method of claim 28 wherein the dry powder comprises particles having a mass median aerodynamic diameter (MMAD) of less than about 3.3 microns.

33. The method of claim 28 wherein the composition has an emitted dose of at least about 30%.

34. The method of claim 28 wherein the composition has an emitted dose of at least about 40%.

35. The method of claim 21 wherein the composition is in aerosolized form.

36. The method of claim 21 wherein the composition further comprises a pharmaceutically acceptable excipient.

37. The method of claim 36 wherein the excipient is a glass-forming excipient.

38. The method of claim 36 wherein the excipient is a carbohydrate.

39. The method of claim 38 wherein the carbohydrate is a sugar.

40. The method of claim 36 wherein the excipient is selected from the group consisting of amino acids, amino acid dimers, amino acid trimers, and polyamino acids.

41. A method of treating or ameliorating diabetes or related conditions comprising administering by inhalation a pharmaceutically effective amount of the composition of claim 1.

42. The method of claim 41 wherein the composition is administered using a dry powder inhaler.

43. The method of claim 41 wherein the composition is administered using a nebulizer.

44. The method of claim 41 wherein the composition is administered using a metered dose inhaler.

45. The method of claim 41 wherein the pharmaceutically effective amount is administered in a plurality of unit dosages.

46. The composition of claim 1, wherein the particles have a mass median diameter (MMD) of less than about 4 µm.

47. The method of claim 21 wherein the particles have a mass median diameter (MMD) of less than about 4 µm.

48. The composition of claim 1, wherein the particles have a mass median diameter (MMD) ranging from 0.1 µm to 5 µm.

49. The method of claim 21, wherein the particles have a mass median diameter (MMD) ranging from 0.1 µm to 5 µm.

* * * * *